United States Patent
Rozzi et al.

(12) 
(10) Patent No.: US 6,733,745 B2
(45) Date of Patent: *May 11, 2004

(54) DEVICES WITH COATINGS CONTAINING CHLORHEXIDINE GLUCONATE, COMPOSITIONS AND METHODS

(75) Inventors: Sharon M. Rozzi, West Lakeland Township, MN (US); Robert A. Asmus, Hudson, WI (US); Brian R. Morrison, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/256,032

(22) Filed: Sep. 26, 2002

(65) Prior Publication Data

US 2003/0138492 A1 Jul. 24, 2003

Related U.S. Application Data

(63) Continuation of application No. 09/089,872, filed on Jun. 4, 1998, now Pat. No. 6,458,341.

(51) Int. Cl.[7] .................................................. A61K 7/22
(52) U.S. Cl. ........................ 424/54; 132/321; 427/2.29; 428/378
(58) Field of Search .......................... 424/54; 132/321; 427/2.29; 428/378

(56) References Cited

U.S. PATENT DOCUMENTS

| | | | |
|---|---|---|---|
| 4,911,927 A | 3/1990 | Hill | 424/443 |
| 5,098,711 A | 3/1992 | Hill | 424/401 |
| 5,165,913 A | 11/1992 | Hill | 424/49 |
| 5,213,803 A | 5/1993 | Pollock et al. | |
| 5,328,698 A * | 7/1994 | Onwumere et al. | 424/486 |
| 5,441,741 A * | 8/1995 | Cheong | 424/402 |
| 5,603,921 A | 2/1997 | Bowen | |
| 5,700,476 A * | 12/1997 | Rosenthal et al. | 424/426 |
| 5,756,552 A * | 5/1998 | Takeuchi et al. | 514/772.2 |

FOREIGN PATENT DOCUMENTS

| | | |
|---|---|---|
| AU | 9464534 | 12/1994 |
| JP | 04 173730 | 6/1992 |
| WO | WO 95/30404 | 11/1995 |

* cited by examiner

Primary Examiner—Frederick Krass
(74) Attorney, Agent, or Firm—Sean J. Edman

(57) ABSTRACT

Devices, coating compositions and methods for making such compositions are provided, wherein the coatings deliver chlorhexidine gluconate from a stable non-aqueous system.

21 Claims, No Drawings

DEVICES WITH COATINGS CONTAINING CHLORHEXIDINE GLUCONATE, COMPOSITIONS AND METHODS

CROSS REFERENCE TO RELATED APPLICATIONS

This application is a continuation of U.S. patent application Ser. No. 09/089,872, filed Jun. 4, 1998, now U.S. Pat. No. 6,458,341.

FIELD OF THE INVENTION

The present invention relates to stable coatings for delivering chlorhexidine gluconate.

BACKGROUND

Chlorhexidine digluconate (commonly known as "chlorhexidine gluconate") is an antimicrobial that is useful for various applications, particularly in the oral environment. Specifically, chlorhexidine gluconate in dental rinses has been clinically proven to reduce gingival inflammation and bleeding. The disadvantages to delivering chlorhexidine gluconate in a rinse are bad taste and staining. Chlorhexidine gluconate is known to decompose to form para-chloroaniline, which is highly toxic.

Hill (U.S. Pat. No. 5,098,711; WO 95/30404; U.S. Pat. Nos. 5,165,913; 4,911,927) describes floss coating compositions with chlorhexidine gluconate. The compositions of Hill contain a surfactant and a coating substance that is insoluble in the surfactant. Optionally, the compositions may contain a humectant like glycerin or polyethylene glycol. In Hill's examples, chlorhexidine gluconate is formed in situ by heating gluconic acid and chlorhexidine free base at high temperature.

Simionato et al (AU 9,464,534) describes putting chemotherapeutic agents in a floss coating composition that contains an emulsifiable wax.

Bowen (U.S. Pat. No. 5,603,921) describes dental floss coating compositions that contain chlorhexidine gluconate and a 2/1 ratio of polyethylene glycol (PEG) 3350/PEG 1000, which are solids at room temperature.

SUMMARY OF THE INVENTION

Devices, coating compositions and methods for preparing coating compositions are provided whereby stable chlorhexidine gluconate may be delivered to the oral environment from an essentially non-aqueous system. The coating comprises chlorhexidine gluconate and a Solubilizing Glycol. The coating additionally comprises a modulus-enhancing component to give proper handling properties. The coating does not contain more than 200 ppm of para-chloroaniline after four weeks at 45° C.

DETAILED DESCRIPTION OF THE INVENTION

As noted above, it is desirable to deliver chlorhexidine gluconate ("CHG") to the oral environment. To date, however, systems have not been adequate to deliver CHG in a format other than in an aqueous rinse in a manner that would also provide stability. CHG degrades to toxic byproducts in a non-aqueous environment, including para-chloroaniline ("PCA") a suspected carcinogen. It is therefore surprising to find that a non-aqueous composition (i.e. having less than about 2% water by weight) may be formulated for stable delivery of CHG to the oral environment.

Non-aqueous coatings of the present invention provide significant advantages in the delivery of CHG. Because the coating does not contain water, it is more shelf-stable for longer term storage since there is no water loss or requirement for special packaging to retain water in the coating.

Coated CHG delivery devices of the present invention, as compared to aqueous rinses, are useful particularly for delivering chlorhexidine gluconate interproximally and subgingivally, where it is needed to treat gingivitis. Site specific delivery of chlorhexidine gluconate from a device, as in the present invention, minimizes the discomfort associated with the bad taste of chlorhexidine gluconate and reduces tooth staining by reducing contact of the chlorhexidine gluconate with the facial tooth surfaces.

The device of the present invention is any device suitable for physical delivery of CHG to the oral environment, and most preferably a device suitable for delivery to interproximal and subgingival surfaces of the oral environment. Such devices include dental floss, dental picks, and dental tape. Additionally, the device may be a dental packing material, such as a fiber. Other embodiments include periodontal membranes.

Dental floss coated with the compositions of the present invention is highly advantageous, because it slips easily between the teeth and yet is easy to hold in the user's hands.

The coating of the present invention comprises chlorhexidine gluconate. CHG may be commercially obtained from many manufacturers, but typically only in an aqueous format. It is important to properly handle aqueous CHG, particularly as to exposure to high temperatures, to retain stability when formulating the non-aqueous compositions of the present invention, as will be described in more detail below.

Preferably, the coating of the present invention comprises between about 0.1% and 15% of CHG by weight. More preferably, the coating comprises 0.5–10%, and most preferably, the coating comprises 1–5% of CHG by weight.

For purposes of the present invention, a "Solubilizing Glycol" is a glycol that provides a clear solution when mixed with CHG in the glycol/CHG ratio to be used in the ultimate coating composition. This evaluation of solution clarity is made to a mixture containing only CHG, glycol and any residual water, after water has been removed to a level less than about 10% and the solution is at room temperature (about 21° C.). It is understood that mechanical mixing under heat as high as 100° C. may be employed to mix the CHG with the glycol, but that the evaluation will be made after the solution has cooled and allowed to stand for 60 minutes.

Examples of glycols capable of dissolving and stabilizing chlorhexidine gluconate are glycerin, sorbitol, polyethylene glycol (preferably of molecular weight between about 200 and 600), polyglycerols (e.g. triglycerol, hexaglycerol and decaglycerol), and propylene glycol. These glycols may be used separately or in combination. It will be recognized that while individual glycols may not provide the desired clear liquid, mixtures of glycols may be suitable to be collectively used as the Solubilizing Glycol.

Solubilizing Glycol is preferably present in the coating in an amount such that the ratio of Solubilizing Glycol to chlorhexidine gluconate by weight is 0.2–200. More preferably the ratio of Solubilizing Glycol to chlorhexidine gluconate by weight is 0.5–7, and most preferably, the ratio is 1–5.

The modulus-enhancing component is any material that provides the desired final modulus properties for the coating, such that it will have the proper tackiness and material delivery properties of a coating. Thus, the coefficient of dynamic friction (ASTM D3247) is preferably less than 2.0 and more preferably less than 1.0. The elastic modulus, G', should be greater than 10,000 and preferably greater than 100,000 dynes/cm$^2$ at a frequency of 1 rad/sec and at room temperature. The ratio of the viscous modulus, G", to G' (or tan delta) should be less than 0.8 and preferably less than 0.5 at a frequency of 1 rad/sec and at room temperature.

Examples of modulus enhancing components include surfactants that contain both (a) hydrophilic group(s) capable of dispersing chlorhexidine gluconate and a glycol, and (b) an alkyl group(s). Preferably the alkyl group makes up 3 to 75% by weight of the modulus-enhancing component, and more preferably 5 to 60 wt. %. Examples of such preferred surfactants include polyglyceryl alkyl esters and ethers, ethoxylated polyhydric alcohol alkyl esters, and polyoxyethylene alkyl ethers or esters. These surfactants may act to bind individual fibers of a dental floss together, or may help in the formulation process to assist in making certain ingredients compatible in the overall coating formulation. Surfactants may be particularly beneficial in assisting wax to be compatible with the rest of the coating composition.

Alternative modulus enhancing components include waxes, poly-n-vinyl pyrrolidone, crystalline fatty alcohols, paraffins, polyethylene oxides having molecular weight greater than about 900, hydroxypropyl cellulose and cellulose derivatives. Preferably, these materials are soluble in or emulsifiable with glycerin.

Wax is particularly preferred in the tooth floss embodiment when it may be desirable to help bind the floss fibers together and to improve the floss handling characteristics. Examples of waxes are microcrystalline wax and beeswax. Alternatively, floss coatings may be formulated such that the fibers are not bound together.

Compositions of the present invention may additionally comprise appropriate adjuvants such as colorants, stabilizers, preservatives, flavorants, sweeteners, additional medicaments (such as fluoride and desensitizers), cleansers and the like.

Salts, acids, and bases that are not to be present in the compositions of the present invention are limited in amount such that they cannot interact with more than 50% of the CHG in the device. In other words, the coating has less than 0.50 molar equivalents of deleterious quantities of salts, acids, and bases that would react with chlorhexidine gluconate based on the amount of chlorhexidine gluconate in the composition. Preferably no more than 0.10 molar equivalents of salts, acids, or bases based on the amount of CHG are in the formulation. More preferably no more than 0.01 molar equivalents, and most preferably no more than 0.001 molar equivalents of salts, acids, or bases based on the amount of CHG are in the formulation.

Examples of salts, acids, and bases that are not to be present in the compositions of the present invention include water soluble or emulsifiable species of the following: carboxylic acids and polycarboxylic acids and their salts (with the exception of gluconic acid and its salts), sulfates, sulfonates, phosphates, phosphonates, acetates, sulfosuccinates, including anionic surfactants utilizing these as hydrophilic groups. Halides, nitrates, hydroxides, carbonates, oxalates, thiocyanates, sulfides, chromates, arsenates, cyanides, chlorates, and iodate salts are also a potential concern. As a general principle, it is desirable to avoid strong acids and strong bases and anionic surfactants, because each of these species tends to adversely react with chlorhexidine gluconate.

It is also desirable that the pH of the composition be maintained between 5 and 8 to provide a more stable system. Due to the anhydrous nature of the material of this invention a convenient method for assessing the relevant pH of the compositions is to dissolve or suspend the material at a 5 to 10% weight basis in pH neutral water and measure the resulting pH.

The stable coating composition of the present invention is made by first mixing aqueous chlorhexidine gluconate with a glycol and optionally with the modulus-enhancing component to form a mixture that is substantially free of deleterious quantities of salts, acids, and bases that would react with the chlorhexidine gluconate. Water is then removed at a temperature less than 100° C., more preferably less than 80° C. and most preferably less than 60° C. Preferably, the water removal operation is conducted under vacuum. The composition is then ready for final formulation (if not all materials in the final formulation have not already been added) and coating on the device. Alternatively, the removal of water may be undertaken after coating a water-containing formulation on the device. While brief periods of exposure of the composition to temperatures above 100° C. may be allowed, extended exposure to high temperature may be seriously deleterious to the stability of the coating composition. It has therefore been surprisingly found that temperature control of the water removal process is extremely important in the production of stable coatings of the present invention.

In an alternative preparation technique, the aqueous chlorhexidine gluconate may be freeze-dried, thereby removing substantially all water from chlorhexidine gluconate in a rapid manner. The thus freeze-dried chlorhexidine gluconate may then be mixed with glycol. The modulus-enhancing component and/or other desired ingredients of the final formulation may be mixed at the same time as the glycol, or as a subsequent formulation operation. The composition is then ready for final formulation (if necessary) and coating on the device.

It particularly desirable to conduct the water removal step under vacuum. This condition allows for use of lower temperatures than would otherwise be required, shorter times at elevated temperatures, and further may facilitate removal of undesirable volatile degradation products or impurities.

The compositions may be coated onto the intended device using appropriate coating techniques, such as dip, melt, extrusion or spray techniques. To facilitate this coating process, it is preferred to formulate the composition such that the melt point of the total composition is about 40–60° C., and more preferably about 40–50° C.

The following examples are provided for purposes of illustrating the present invention, and are not intended to limit to broadest concepts of the present invention. Unless otherwise specified, all parts and percentages are by weight, and molecular weights are number average.

EXAMPLES

Example 1

A stock solution of 2/1 glycerin/chlorhexidine gluconate (CHG) was prepared by dissolving 2 parts of glycerin (Aldrich Chemical Company, Milwaukee, Wis.) in 5 parts of 20 wt. % CHG in water (Medichem S. A., Barcelona, Spain). The water from this solution was removed under vacuum and at 60° C. using a Rotavapor R110 (Buchi, Germany).

A stock solution of 2/1 polyethylene glycol ("PEG-400", molecular weight 400)/chlorhexidine gluconate (CHG) was prepared by dissolving 2 parts of PEG-400 (Aldrich Chemical Company) in 5 parts of 20 wt. % CHG in water. The water from this solution was removed under vacuum and at 60° C. using a Rotavapor R110.

Floss coating compositions were prepared per Table 1. All Example 1 samples were made by melting 94 parts of surfactant at approximately 50° C., and then adding and dispersing 6 parts of the 2/1 stock solution of either glycerin/CHG or PEG-400/CHG. Uncoated dental floss (Hi-Tech floss, Ranir-DCP Corporation, Grand Rapids, Mich.) was dip-coated into the molten CHG dispersions. The excess coating was removed with a tongue depressor while still molten.

The release rate of CHG from the coated floss samples was measured by high pressure liquid chromatography (HPLC). Samples were prepared by placing a 2-inch floss segment of known coating weight and into deionized water in a 2 dram vial. The vials were shaken for ten minutes on a paint shaker (Red Devil, Inc., Union, N.J.). The floss segment was then removed from each vial, and the concentration of CHG in the water was determined per the test method summarized below. The percentage of the CHG in the floss that was released into the water was calculated from the initial coating weight and the water CHG concentration.

HPLC Test Method for Determining CHG Concentration
Equipment:
1. A Hewlett Packard 1090 HPLC.
2. Detector: Diode Array at 205 nm.
3. Column: Prodigy 5 ODS 3, 100 Å pore size, 5 mm particle size, silica-based C18 column, 4.6×150 mm (Phenomenex, Inc., Torrance, Calif.).
4. HPLC grade Acetonitrile (J. T. Baker Inc., Phillipsburg, N.J.)
5. Deionized water.
6. Triethylamine (99%, Aldrich Chemical Company).
7. 85% Phosphoric Acid (J. T. Baker Inc.).
8. Buffer Filter: Empore filter (3M Company, St. Paul, Minn.).
9. Automatic pipette and pipette tips: 0.1–1 mL.
10. HPLC vials with caps (Fisher Scientific, Pittsburgh, Pa.).

Procedure:
1. The following CHG standards were prepared in deionized water: 0.005%, 0.003%, 0.001%, 0.0007%, and 0.0005% (w/v).
2. HPLC vials were filled with the prepared samples and CHG standards. The vials were loaded into the HPLC.
3. The mobile phase was prepared using the following procedure:
   a) Deionized water (1000 mL) was placed in a beaker.
   b) Stirring was initiated, and a pH meter was placed in the beaker for continuous measurement.
   c) Triethylamine (10 mL) was allocated into the beaker.
   d) Phosphoric acid was added dropwise until the pH was 2.5.
   e) The mobile phase was filtered through a 3M Empore filter.
4. HPLC test parameters:
   a) Flow Rate: 1.0 mL/min.
   b) Mobile Phase: 75% 1.0% Triethylamine/phosphate at pH 2.5 and 25% acetonitrile.
   c) Temperature: room temperature (21° C.).
   d) Injection volume: 24 $\mu$L.
   e) Draw speed: 83 $\mu$L/min.
   f) Injections/vial: 2–3.
   g) Diode Array Detector: sample at 205 nm with a bandwidth of 4 nm, reference at 500 nm with a bandwidth of 50 nm.
5. Samples and standards were run though the HPLC.
6. A calibration curve of CHG concentration versus peak area was generated from the results of the standard solutions.
7. The concentration of CHG in the water of each sample was determined from the calibration curve.

The release rate of CHG from the coated floss samples are listed in Table 1. The results show that the floss compositions of the present invention give excellent release of CHG in an aqueous environment.

TABLE 1

Floss Coating Compositions and CHG release rate in water.

| Example | Surfactant | Glycol | Coating Weight (mg) | Water for Release Test (ml) | Percent of CHG in floss released |
|---|---|---|---|---|---|
| 1A | PEG-150 Distearate ("CDS-6000P", Nikkol Chemical Company, Japan) | Glycerin | 13.9 | 10 | 60.0 |
| 1B | CDS-6000 | PEG-400 | 15.6 | 10 | 43.3 |
| 1C | Polyglyceryl-10 Tristearate ("Decaglyn 3-S" Nikkol) | Glycerin | 15.1 | 10 | 17.9 |
| 1D | Decaglyn 3-S | PEG-400 | 11.8 | 10 | 28.5 |
| 1E | PEG-40 Stearate ("Emerest 2715", Henkel Corporation, Hoboken, New Jersey) | Glycerin | 12.7 | 10 | 31.9 |
| 1F | Emerest 2715 | PEG-400 | 5.6 | 5 | 69.2 |
| 1G | "Unithox 380" (an ethoxylate alcohol; 80% PEG, 20% C24; Baker Petrolite Corporation, LaGrange, IL) | Glycerin | 8.6 | 5 | 12.8 |
| 1H | Unithox 380 | PEG-400 | 7.1 | 5 | 16.3 |

Example 2

Floss coatings were prepared per the compositions listed in Table 2 using the following procedure. Each surfactant was melted at approximately 50° C., and then the required quantity of either the 2/1 glycerin/CHG stock solution of Example 1 or the 2/1 PEG-400/CHG stock solution of Example 1 was added and dispersed with stirring. Uncoated Hi-Tech dental floss was dip-coated into the molten coating dispersions. The excess coating was removed with a tongue depressor while still molten.

The release rate of CHG from the coated floss samples was measured using the following procedure. One inch floss segments of known coating weight were placed in individual ½ dram vials with 1 mL of deionized water. The vials were shaken for ten minutes on a paint shaker. The floss segment was then removed from each vial, and the concentration of CHG in the water was determined per the HPLC test method of Example 1. The percentage of the CHG in the floss that was released into the water was calculated from the initial coating weight and the water CHG concentration. The test results summarized in Table 2 represent the average of three replicate measurements. The results in Table 2 show that the floss compositions of the present invention give excellent release of CHG in an aqueous environment.

TABLE 2

Compositions of Examples 2A–2F and CHG release rate in water.

| Example | Surfactant | Glycol | Glycol (wt. %) | CHG in Coating (wt. %) | Percent of CHG in floss released |
|---|---|---|---|---|---|
| 2A | Polyglyceryl-2 Stearate ("DGMS", Nikkol) | PEG-400 | 4.04 | 2.02 | 65.57 |
| 2B | DGMS | Glycerin | 4.16 | 2.08 | 70.03 |
| 2C | Polyglyceryl-10 Distearate ("Decaglyn 2-S", Nikkol) | PEG-400 | 3.94 | 1.97 | 52.43 |
| 2D | Decaglyn 2-S | Glycerin | 4.22 | 2.11 | 33.32 |
| 2E | Polyglyceryl-4 Stearate ("Tetraglyn 1-S", Nikkol) | PEG-400 | 3.98 | 1.99 | 40.10 |
| 2F | Tetraglyn 1-S | Glycerin | 4.40 | 2.20 | 32.53 |

Example 3

Stock solutions of glycerin/CHG were prepared in the following ratios using the procedure described in Example 1: 1.5/1 and 0.5/1.

Floss coatings with the surfactant Unithox 380 were prepared per the compositions listed in Table 3. The required quantity of Unithox 380 was melted at approximately 50° C., and then the required quantity of one of the two glycerin/CHG stock solutions above was added and dispersed with stirring. The floss coatings were aged for four weeks at 45° C. and then the concentration of para-chloroaniline (PCA), a by-product of CHG decomposition, was determined using the HPLC method described below. Water was used as the sample solvent in the test method to effect dissolution. The PCA concentration results are listed in Table 3. The results show the compositions of the present invention have good stability (PCA<200 PPM).

TABLE 3

Compositions of Examples 3A–3B, and Concentration of PCA after 4 weeks at 45° C.

| | Initial Coating Composition | | | | |
|---|---|---|---|---|---|
| Example | Glycerin/ CHG | Glycerin (wt. %) | CHG (wt. %) | Unithox 380 (wt. %) | PCA after 4 weeks at 45° C. (ppm) |
| 3A | 1.5 | 3.06 | 2.04 | 94.90 | 43 |
| 3B | 0.5 | 1.03 | 2.05 | 96.93 | 15 |

HPLC Test Method for Determining both PCA and CHG Concentration in Floss Coating Equipment:
1. A Hewlett Packard 1090 HPLC.
2. Detector: Diode Array at 205 nm.
3. Column: Supelcosil ABZ+Plus silica-based alkyl amide chain column, 5 micron, 4.6×150 mm (Supelco, Inc., Bellefonte, Pa.).
4. Column Prefilter: 2 cm Supelguard Cartridge and stand-alone holder designed for 5 micron Supelcosil column (Supelco, Inc.).
5. Para-chloroaniline (Aldrich Chemical Company).
6. HPLC grade Acetonitrile.
7. Deionized water.
8. Triethylamine.
9. 85% Phosphoric Acid.
10. Buffer Filter: 3M Empore filter.
11. Automatic pipette and pipette tips: 0.1–1 mL.
12. HPLC vials with caps.
13. Ultrasonic bath with temperature control: Branson 2210 (Branson Ultrasonics Corp., Danbury, Conn.).
14. Glacial acetic acid (Aldrich Chemical Company).
15. Sample Filter: Anotop Plus syringe filter, 25 mm diameter, 0.2 micron pore size plus integral prefilter (Whatman International Ltd., Maidstone, England).
16. Chlorhexidine free base (Aldrich Chemical Company).

Procedure:
1. The following chlorhexidine free base (CHFB) standards were prepared in deionized water using acetic acid to aid in dissolution: 0.01%, 0.007%, 0.005%, 0.003%, 0.001%, 0.0007 and 0.0005% (w/v).
2. The following para-chloroaniline standards were prepared in HPLC grade acetonitrile: 0.01%, 0.008%, 0.004%, 0.001%, 0.0001%, 0.00007% (w/v).
3. The samples for PCA and CHG concentration determination were prepared as follows:
    a) Coating samples were melted at 50° C. in an ultrasonic bath and stirred to ensure homogeneity.
    b) The coating samples were resolidified at room temperature, and then 0.5 gms was placed in a 10 mL volumetric flask.
    c) An effective solvent for each sample was charged to the volumetric flask to the 10 mL graduation mark.
    d) The volumetric flask was sonicated in the ultrasonic bath for ten minutes to effect dissolution of the floss coating in the solvent.
    e) The sonicated solutions were filtered with an Anotop 25 Plus syringe filter.
4. HPLC vials were filled with the prepared samples and standards. The vials were loaded into the HPLC.

5. The mobile phase was prepared using the following procedure:
   a) Deionized water (1000 mL) was placed in a beaker.
   b) Stirring was initiated, and a pH meter was placed in the beaker for continuous measurement.
   c) Triethylamine (10 mL) was allocated into the beaker.
   d) Phosphoric acid was added dropwise until the pH was 3.0.
   e) The mobile phase was filtered through a 3M Empore filter.
6. HPLC test parameters:
   a) Flow Rate: 1.0 mL/min.
   b) Mobile Phase: 67% 1.0% Triethylamine/phosphate at pH 3.0 and 33% acetonitrile.

Example 4

Floss coatings were prepared per the compositions listed in Table 4. Approximately 94 parts of surfactant was melted at approximately 50° C. Approximately 6 parts of either the 2/1 glycerin/CHG stock solutions of Example 1 or the 2/1 PEG-400/CHG stock solution of Example 1 was added and dispersed with stirring. The floss coating samples were aged for twelve weeks at 37° C. and 45° C., after which the concentration of PCA was determined using the HPLC method of Example 3. The PCA concentration results are listed in Table 4.

TABLE 4

Compositions of Examples 4A–4O, and Concentration of PCA after Aging for 12 weeks at 37° C. and 45° C.

| | | | Initial Coating Composition | | PCA Concentration in Coating (ppm) | |
|---|---|---|---|---|---|---|
| Example | Surfactant | Glycol | Glycol (wt. %) | CHG (wt. %) | After 12 weeks at 37° C | After 12 weeks at 45° C. |
| 4A | DGMS | Glycerin | 4.04 | 2.02 | 16 | 93 |
| 4B | DGMS | PEG 400 | 4.20 | 2.10 | 38 | 180 |
| 4C | Decaglyn 3-S | Glycerin | 4.00 | 2.00 | 110 | 170 |
| 4D | Decaglyn 3-S | PEG 400 | 4.06 | 2.03 | 251 | 729 |
| 4E | Tetraglyn 1-S | Glycerin | 4.04 | 2.02 | 38 | 94 |
| 4F | Tetraglyn 1-S | PEG 400 | 3.98 | 1.99 | 104 | 120 |
| 4G | Decaglyn 2-S | Glycerin | 4.00 | 2.00 | 13 | 553 |
| 4H | Decaglyn 2-S | PEG 400 | 3.98 | 1.99 | 94 | 395 |
| 4I | Decaglyn 1-S | Glycerin | 4.00 | 2.00 | 1993 | 1262 |
| 4J | Unithox 380 | Glycerin | 4.00 | 2.00 | 1783 | 982 |
| 4K | Unithox 380 | PEG 400 | 4.06 | 2.03 | 54 | 83 |
| 4L | Emerest 2715 | Glycerin | 4.00 | 2.00 | 317 | 31 |
| 4M | Emerest 2715 | PEG 400 | 4.22 | 2.11 | 40 | 26 |
| 4N | CDS-6000P | Glycerin | 4.06 | 2.03 | 1099 | 1164 |
| 4O | CDS-6000P | PEG 400 | 4.00 | 2.00 | 1056 | 1605 | d) Temperature: room temperature (21° C.).
   e) Injection volume: 24 µL.
   f) raw speed: 83 µL/min.
   g) Injections/vial: 2.
   h) Diode Array Detector: sample at 205 nm with a bandwidth of 4 nm, reference at 500 nm with a bandwidth of 50 nm.
7. Samples and standards were run though the HPLC.
8. A calibration curve of CHFB concentration versus peak area was generated from the results of the CHFB standard solutions.
9. The CHFB concentration in each sample solution was determined from the calibration curve. The CHFB solution concentration was converted to a CHG solution concentration.
10. The CHG concentration in the floss coating was determined from the CHG solution concentration.
11. A calibration curve of PCA concentration versus peak area was generated from the results of the PCA standard solutions.
12. The PCA concentration in each sample solution was determined from the calibration curve.
13. The PCA concentration in the floss coating was determined from the PCA solution concentration.

Example 5 and Comparative Example 1

Comparison of Example 5 and Comparative Example 1 shows that the compositions of the present invention are more stable to CHG decomposition than the compositions of Bowen (U.S. Pat. No. 5,603,921). The compositions of Bowen contain CHG and 2/1 PEG-3350/PEG-1000. Comparative Example 1 of Bowen was made by melting 31.7 parts of PEG-1000 (Dow Chemical Company, Midland, Mich.) and adding 25 parts of aqueous CHG (20 wt. %). The water from this solution was removed under vacuum at 60° C. using a Rotavapor R110. To this water-free solution was added 63.4 parts of melted PEG-3400 (Aldrich Chemical Company). The resultant composition of Comparative Example 1 was 5 wt. % CHG, 63.4 wt. % PEG-3350, and 31.7 wt. % PEG-1000, and was a solid at room temperature.

The floss coating of Example 5 was made using the following procedure. A stock solution of 1/1 PEG-400/CHG was prepared by dissolving 1 part of PEG-400 in 5 parts of 20 wt. % CHG in water. The water from this solution was removed under vacuum at 60° C. using a Rotavapor R110. Ten parts of this stock solution was dispersed in 90 parts of melted Unithox 380 at approximately 50° C. The resultant composition of Example 5 was 5 wt. % CHG, 5 wt. % PEG-400, and 90 wt. % Unithox 380.

The floss coating samples of Example 5 and Comparative Example 1 were aged at 45° C. for four weeks, and then the coatings were analyzed for PCA concentration per the test method of Example 3. The results are listed in Table 5. The results show that the PCA concentration of Example 5 is lower than that Comparative Example 1. These results show that the compositions of the present invention are better at stabilizing CHG than those of Bowen.

prepared per the procedure described by Hill in Example 61, and that procedure is described below.

TABLE 6

Compositions of Comparative Example 2 Floss Coatings (from Hill, U.S. Pat. No. 5,098,711, Example 61, Table XI).

| | Comparative Example | Pluronic F-127 | Silicone | Saccharin | Flavor | Carageenan | Silica | Sorbitol | Chlorhexidine as free base CHFB | as CHG | Total |
|---|---|---|---|---|---|---|---|---|---|---|---|
| Parts | 2A | 65 | 15 | 2 | 5 | 7 | 6 | 0 | 0.4 | 0.710 | 100.71 |
| | 2B | 55 | 15 | 1 | 7 | 0 | 7 | 15 | 0.2 | 0.355 | 100.36 |
| | 2C | 57.5 | 12.5 | 2 | 10 | 2 | 5 | 11 | 0.4 | 0.710 | 100.71 |
| | 2D | 65 | 15 | 2 | 0 | 7 | 6 | 0 | 0.4 | 0.710 | 95.71 |
| | 2E | 55 | 15 | 1 | 0 | 0 | 7 | 15 | 0.2 | 0.355 | 93.36 |
| | 2F | 57.5 | 12.5 | 2 | 0 | 2 | 5 | 11 | 0.4 | 0.710 | 90.71 |
| Wt. % | 2A | 64.541 | 14.894 | 1.986 | 4.965 | 6.951 | 5.958 | 0.000 | 0.397 | 0.705 | 100.00 |
| | 2B | 54.805 | 14.947 | 0.996 | 6.975 | 0.000 | 6.975 | 14.947 | 0.199 | 0.354 | 100.00 |
| | 2C | 57.094 | 12.412 | 1.986 | 9.929 | 1.986 | 4.965 | 10.922 | 0.397 | 0.705 | 100.00 |
| | 2D | 67.913 | 15.672 | 2.090 | 0.000 | 7.314 | 6.269 | 0.000 | 0.418 | 0.742 | 100.00 |
| | 2E | 58.915 | 16.068 | 1.071 | 0.000 | 0.000 | 7.498 | 16.068 | 0.214 | 0.381 | 100.00 |
| | 2F | 63.388 | 13.780 | 2.205 | 0.000 | 2.205 | 5.512 | 12.126 | 0.441 | 0.783 | 100.00 |
| Wt. (g) | 2A | 32.271 | 7.447 | 0.993 | 2.482 | 3.475 | 2.979 | 0.000 | 0.199 | 0.353 | 50.00 |
| | 2B | 27.403 | 7.473 | 0.498 | 3.488 | 0.000 | 3.488 | 7.473 | 0.100 | 0.177 | 50.00 |
| | 2C | 28.547 | 6.206 | 0.993 | 4.965 | 0.993 | 2.482 | 5.461 | 0.199 | 0.353 | 50.00 |
| | 2D | 33.957 | 7.836 | 1.045 | 0.000 | 3.657 | 3.134 | 0.000 | 0.209 | 0.371 | 50.00 |
| | 2E | 29.457 | 8.034 | 0.536 | 0.000 | 0.000 | 3.749 | 8.034 | 0.107 | 0.190 | 50.00 |
| | 2F | 31.694 | 6.890 | 1.102 | 0.000 | 1.102 | 2.756 | 6.063 | 0.220 | 0.392 | 50.00 |

TABLE 5

Stability Studies of Example 5 and Comparative Example 1: PCA after Aging at 4 weeks at 45° C.

| | Concentration of PCA (ppm) after 4 weeks at 45° C. |
|---|---|
| Comparative Example 1 | 283 |
| Example 5 | 30 |

Comparative Example 2

Comparison of the floss coatings of Comparative Example 2 and Example 6 shows that the compositions of the present invention give better release of CHG and are more stable to CHG decomposition than the compositions of Hill (U.S. Pat. No. 5,098,711).

The chlorhexidine gluconate-containing examples of Hill are described in Example 61 and Table XI of U.S. Pat. No. 5,098,711. These three compositions were reproduced to the best of our ability, but our efforts were hampered by our inability to trace the flavor "IFF 101". IFF is the acronym for International Flavors and Fragrances, Inc. of Dayton, N.J., but they do not presently have a product named IFF 101. The authors reproduced the three Hill examples both with a substitute flavor (PFC 9894 peppermint flavor, Foote & Jenks, Inc., Camden, N.J.) (Comparative Examples 2A–2C), and without a flavor (Comparative Examples 2D–2F). The compositions of Comparative Examples 2A–2F are described in Table 6 below. Table 6 is organized in a manner similar to Table XI of Hill U.S. Pat. No. 5,098,711 to facilitate comparison. Comparative Examples 2A–2F were In the Hill examples chlorhexidine gluconate is formed in situ by preparing gluconic acid and reacting it with chlorhexidine free base. D-glucono-d-lactone (Aldrich Chemical Company) (1.09 g) was moistened with an excess of water (0.65 g) and heated to 75° C. for 15 minutes in a closed vessel to convert it to gluconic acid. To this gluconic acid, surfactant Pluronic F-127 (BASF Corp., Parsippany, N.J.) (120 g) was added to make a 1% gluconic acid mixture if all the lactone was converted. This mixture was heated to 150° C. to melt the Pluronic F-127 and effect mixing.

Table 7 describes the quantities of chlorhexidine free base, gluconic acid and Pluronic F-127 that were combined for each Comparative Example 2A–2F. Pluronic F-127 was melted at 150° C., and then mixed with chlorhexidine free base (Aldrich). To this chlorhexidine free base solution was added the gluconic acid/Pluronic F-127 mixture such that the molar ratio of gluconic acid to chlorhexidine free base was 2.25 to 1 (same as in Hill). This mixture was stirred at 150° C. to effect the reaction to chlorhexidine gluconate. Hill does not specify how long to carry-out this reaction. For Comparative Example 2A this reaction was carried out for 30 minutes after which time the color of the mixture changed from white to light brown which would indicate some decomposition of CHG. For Comparative Examples 2B–2F this reaction of chlorhexidine free base and gluconic acid was carried out for 10 minutes which resulted in only a slight color change.

After the above reaction time, each mixture was cooled to 120° C., which was determined to be the lowest temperature possible to produce a smooth melt. The remaining floss coating components were added per the quantities in Table 6. The silicone ("Dow Corning Silicone 1500", Dow Corning Corp., Midland, Mich.) was added until a thick cream was formed, after which the sorbitol and saccharin (both from Aldrich Chemical Company) were added. Next the carageenan (Aldrich Chemical Company) and silica ("Sil-So-Sil 45", U.S. Silica, Ottawa, Ill.) were charged and mixed. Lastly, the flavor was added and mixed to reduce volatilization of the oil. Uncoated Hi-Tech floss was dip-coated into the molten floss coatings. The excess coating was removed by passing the floss through a 0.006 inch slit die while the coating was still molten.

TABLE 7

Quantities of chlorhexidine free base, gluconic acid and Pluronic F-127 that were combined for Comparative Examples 2A–2F.

| | | | | Weights (gm) | | |
|---|---|---|---|---|---|---|
| Comparative Example | CHG Desired | CHFB Needed | Gluconic Acid Needed | Gluconic Acid + F-127 Mixture Added | Pluronic F-127 Used to dissolve CHFB | Total Pluronic F-127 |
| 2A | 0.353 | 0.199 | 0.173 | 17.500 | 14.944 | 32.271 |
| 2B | 0.177 | 0.100 | 0.087 | 8.781 | 18.709 | 27.403 |
| 2C | 0.353 | 0.199 | 0.173 | 17.500 | 11.220 | 28.547 |
| 2D | 0.371 | 0.209 | 0.182 | 18.414 | 15.725 | 33.957 |
| 2E | 0.190 | 0.107 | 0.093 | 9.439 | 20.111 | 29.457 |
| 2F | 0.392 | 0.220 | 0.192 | 19.429 | 12.457 | 31.694 |

Example 6

Floss coating compositions with the same concentrations of CHG as those of Comparative Example 2 were prepared per Table 8. The compositions were prepared by melting the surfactant at approximately 50° C., and then adding and dispersing the required amount of the 2/1 glycerin/CHG stock solution of Example 1. Uncoated Hi-Tech floss was dip-coated into the molten floss coatings. The excess coating was removed by passing the floss through a 0.006 inch slit die while the coating was still molten.

TABLE 8

Compositions of Examples 6A–6J

| | | Weight Percent | | | Weight (gm) | | |
|---|---|---|---|---|---|---|---|
| Example | Surfactant | Surfactant | Glycerin | CHG | Surfactant | Glycerin | CHG |
| 6A | Unithox 380 | 97.885 | 1.410 | 0.705 | 19.577 | 0.282 | 0.141 |
| 6B | Unithox 380 | 98.938 | 0.708 | 0.354 | 19.788 | 0.142 | 0.071 |
| 6C | Unithox 380 | 97.774 | 1.484 | 0.742 | 19.555 | 0.297 | 0.148 |
| 6D | Unithox 380 | 98.857 | 0.762 | 0.381 | 19.771 | 0.152 | 0.076 |
| 6E | Unithox 380 | 97.651 | 1.566 | 0.783 | 19.530 | 0.313 | 0.157 |
| 6F | Decaglyn 3-S | 97.885 | 1.410 | 0.705 | 19.577 | 0.282 | 0.141 |
| 6G | Decaglyn 3-S | 98.938 | 0.708 | 0.354 | 19.788 | 0.142 | 0.071 |
| 6H | Decaglyn 3-S | 97.774 | 1.484 | 0.742 | 19.555 | 0.297 | 0.148 |
| 6I | Decaglyn 3-S | 98.857 | 0.762 | 0.381 | 19.771 | 0.152 | 0.076 |
| 6J | Decaglyn 3-S | 97.651 | 1.566 | 0.783 | 19.530 | 0.313 | 0.157 |

The release rate of CHG from the coated floss samples of Example 6 and Comparative Example 2 was measured using the following procedure. Samples were prepared by placing 3 to 10 inches of floss of known coating weight and 1 mL of deionized water into a ½ dram vial. The floss length used for each composition was such that if all of the initial chlorhexidine (calculated as CHFB) charged to the coating were released, the concentration in solution would be equivalent to the most concentrated CHFB standard (0.01 (w/v) %). The vials were shaken for ten minutes on a paint shaker. The floss was then removed from each vial, the remaining sample was filtered with an Anotop 25 Plus syringe filter, and the concentration of CHG in the water was determined per the HPLC test method of Example 3. The percentage of the CHG in the floss that was released into the water was calculated from the initial coating weight and the water CHG concentration. Each composition was tested in triplicate. The test results summarized in Table 9 represent the average of the three measurements. The compositions in Table 9 are grouped by the CHG concentration in the floss coating to facilitate comparison. The results show that the floss compositions of the present invention give better release of CHG in an aqueous environment than those of Hill.

TABLE 9

CHG release rate in water for Example 6 and Comparative Example 2.

| Example | CHG in Floss Coating (wt. %) | Percent of CHG in floss released |
|---|---|---|
| Comparative Example 2A | 0.705 | <5.9 |
| Comparative Example 2C | 0.705 | <5.3 |

TABLE 9-continued

CHG release rate in water for Example 6 and Comparative Example 2.

| Example | CHG in Floss Coating (wt. %) | Percent of CHG in floss released |
|---|---|---|
| Example 6A | 0.705 | 66.3 |
| Example 6F | 0.705 | 7.1 |
| Comparative Example 2B | 0.354 | <4.8 |
| Example 6B | 0.354 | 39.2 |
| Example 6G | 0.354 | 6.7 |
| Comparative Example 2D | 0.742 | <4.7 |
| Example 6C | 0.742 | 90.4 |
| Example 6H | 0.742 | 6.1 |
| Comparative Example 2E | 0.381 | <4.9 |
| Example 6D | 0.381 | 23.6 |
| Example 6I | 0.381 | 6.6 |
| Comparative Example 2F | 0.783 | <4.7 |
| Example 6E | 0.783 | 88.3 |
| Example 6J | 0.783 | 9.0 |

The floss coating samples of Example 6 and Comparative Example 2 were aged at 45° C. for four weeks, and then the coatings were analyzed for PCA concentration per the test method of Example 3. The results are listed in Table 10. The compositions in Table 10 are grouped by the initial CHG concentration in the floss coating to facilitate comparison. For every initial CHG concentration, the PCA concentration in the floss coatings of Comparative Example 2 was significantly higher than that of the floss coatings of Example 6. These results show that the compositions of the present invention are better at stabilizing CHG than those of Hill.

TABLE 10

Stability Studies of Example 6 and Comparative Example 2: PCA Concentration after 4 weeks at 45° C.

| Example | Initial CHG in Floss Coating (wt. %) | Concentration of PCA in Coating after 4 weeks at 45° C. (ppm) |
|---|---|---|
| Comparative Example 2A | 0.705 | 22399 |
| Comparative Example 2C | 0.705 | 16986 |
| Example 6A | 0.705 | 41 |
| Example 6F | 0.705 | 74 |
| Comparative Example 2B | 0.354 | 7928 |
| Example 6B | 0.354 | 22 |
| Example 6G | 0.354 | 21 |
| Comparative Example 2D | 0.742 | 19636 |
| Example 6C | 0.742 | 37 |
| Example 6H | 0.742 | 21 |
| Comparative Example 2E | 0.381 | 10165 |
| Example 6D | 0.381 | 23 |
| Example 6I | 0.381 | 22 |
| Comparative Example 2F | 0.783 | 15947 |
| Example 6E | 0.783 | 73 |
| Example 6J | 0.783 | 22 |

Example 7

Floss coatings were prepared per the compositions listed in Table 11. Appropriate amounts (depending on compositions described in Table 11) of the surfactant Decaglyn 2-S were melted at approximately 50° C.

1/1 stock solutions of glycerin/CHG and PEG400/CHG were prepared using the procedures described in Example 1. Additional glycerin or PEG400 was added to each composition to obtain the appropriate ratios of glycol to CHG described in Table 11.

The glycol/CHG solutions were added to the melted surfactants and dispersed with stirring. The floss coating samples were aged for four weeks at 45° C., after which the concentration of PCA was determined using the HPLC method of Example 3. The PCA concentration results are listed in Table 11. The results show the compositions of the present invention have good stability (PCA<200 ppm).

TABLE 11

Compositions of Examples 7A–7N, and Concentration of PCA after Aging for 4 weeks at 45° C.

| Example | Glycol | Surfactant (wt %) | Glycol (wt %) | CHG (wt %) | Concentration of PCA (ppm) 45° C., 4 weeks |
|---|---|---|---|---|---|
| 7A | Glycerin | 94 | 5 | 1 | 14.6 |
| 7B | Glycerin | 89 | 10 | 1 | 11.2 |
| 7C | Glycerin | 90 | 5 | 5 | 116.8 |
| 7D | Glycerin | 85 | 10 | 5 | 127.4 |
| 7E | PEG400 | 94 | 5 | 1 | 4.2 |
| 7F | PEG400 | 89 | 10 | 1 | 7.0 |
| 7G | PEG400 | 90 | 5 | 5 | 86.1 |
| 7H | PEG400 | 85 | 10 | 5 | 73.3 |
| 7I | Glycerin | 89.5 | 7.5 | 3 | 34.9 |
| 7J | PEG400 | 89.5 | 7.5 | 3 | 22.0 |
| 7K | Glycerin | 89.5 | 7.5 | 3 | 55.7 |
| 7L | PEG400 | 89.5 | 7.5 | 3 | 25.8 |
| 7M | Glycerin | 89.5 | 7.5 | 3 | 31.8 |
| 7N | PEG400 | 89.5 | 7.5 | 3 | 18.3 |

Example 8

Examples 8A–8C were prepared by melting 89.5 parts of surfactant (per Table 12) at approximately 50° C., and then dispersing 4.5 parts of glycerin and 6 parts of a 1/1 stock solution of glycerin/CHG (prepared per the procedure of Example 1). The surfactant "MYS-40" is PEG-40 stearate from Nikkol.

The elastic (G') and viscous (G") modulus of Examples 7I, and 8A–8C were determined using a controlled-strain rheometer ("RDA-2" from Rheometrics Scientific Inc., Piscataway, N.Y.). Measurements were made at room temperature (25° C.) with a parallel plate geometry (25 mm diameter, gap of 2 mm) with a strain of 0.01% and a frequency of 1 rad/sec. The results are shown in Table 12 including the ratio of G" to G' which is tan δ.

TABLE 12

Rheological Studies of Examples 7I, and 8A–8C at Room Temperature and a Frequency of 1 rad/sec.

| Example | Surfactant | G' (dynes/cm$^2$) | G" (dynes/cm$^2$) | tan δ |
|---|---|---|---|---|
| 7I | Decaglyn 2-S | 1.30E+07 | 5.22E+06 | 0.402 |
| 8A | Emerest 2715 | 6.10E+06 | 1.57E+06 | 0.257 |
| 8B | Unithox 380 | 3.00E+05 | 3.47E+04 | 0.116 |
| 8C | MYS-40 | 1.13E+07 | 1.52E+06 | 0.135 |

Example 9

Floss coatings were prepared per the compositions listed in Table 13. For Example 9A, approximately 89.5 parts of the surfactant Emerest 2715 was melted at approximately 50° C. For Examples 9B–9G, approximately 84.5 parts of the surfactant Emerest 2715 was melted at approximately 50° C.

A 2.5/1 stock solution of glycerin/CHG was prepared using the procedure described in Example 1. Approximately 10.5 parts of this stock solution was added to each of the melted surfactants and dispersed with stirring.

Flavorants (5 parts) were added to Examples 9B–9G. The flavorants respectively used were SN026928 peppermint (International Flavors & Fragrances Inc., Dayton, N.J.), SN026929 peppermint (International Flavors & Fragrances Inc.), SN026930 wintergreen (International Flavors & Fragrances Inc.), SN026943 peppermint (International Flavors & Fragrances Inc.), SN026944 peppermint (International Flavors & Fragrances Inc.), and PFC 9831 peppermint (Foote & Jenks, Canden, N.J.).

The floss coating samples were aged for 4 weeks at 37° C., after which the concentration of PCA was determined using the HPLC method described in Example 3. The PCA concentration results are listed in Table 13. The results show the compositions of the present invention have good stability.

TABLE 13

Compositions of Examples 9A–9G, and Concentration of PCA after Aging for 4 Weeks at 37° C.

| Example | Flavorant | Surfactant (wt %) | Glycerin (wt %) | CHG (wt %) | Flavorant (wt %) | Concentration of PCA (ppm) 37° C., 4 weeks |
|---|---|---|---|---|---|---|
| 9A | None | 89.57 | 7.45 | 2.98 | 0.00 | 2.0 |
| 9B | SN026928 | 84.52 | 7.46 | 2.98 | 5.04 | 1.9 |
| 9C | SN026929 | 84.32 | 7.55 | 3.02 | 5.10 | 1.6 |
| 9D | SN026930 | 84.50 | 7.51 | 3.00 | 4.99 | 1.8 |
| 9E | SN026943 | 84.35 | 7.61 | 3.04 | 5.00 | 1.5 |
| 9F | SN026944 | 84.43 | 7.55 | 3.02 | 4.99 | 1.7 |
| 9G | PFC 9831 | 84.45 | 7.56 | 3.02 | 4.97 | 1.5 |

What is claimed:

1. A device for delivering chlorhexidine gluconate to the oral environment, said device comprising a coating comprising:
   a) chlorhexidine gluconate
   b) Solubilizing Glycol, and
   c) a surfactant that contains both (a) hydrophilic group(s) capable of dispersing chlorhexidine gluconate and a glycol, and (b) an alkyl group(s), said coating comprising no more than about 2% water by weight and having less than 0.5 molar equivalents of deleterious quantities of salts, acids, and bases that would react with chlorhexidine gluconate based an the amount of chlorhexidine gluconate in the coating, and said coating containing no more than 200 ppm of PCA after four weeks at 45° c.

2. The device of claim 1, wherein said surfactant is selected from the group consisting of polyglyceryl alkyl esters and ethers, ethoxylated polyhydric alcohol alkyl esters, and polyoxyethylene alkyl ethers or esters.

3. The device of claim 1, wherein said Solubilizing Glycol is glycerin.

4. The device of claim 1, wherein said Solubilizing Glycol is selected from the group consisting of glycerin, sorbitol, polyethylene glycol, polyglycerols, propylene glycol and mixtures thereof.

5. The device of claim 1, wherein chlorhexidine gluconate is present in the coating as at least 0.1% by weight, and Solubilizing Glycol is present in the coating in an amount such that the ratio of Solubilizing Glycol/chlorhexidine gluconate by weight is 0.2–200.

6. The device of claim 1, wherein said coating further comprises a modulus-enhancing component selected from the group consisting of waxes, poly-n-vinyl pyrrolidone, crystalline fatty alcohols, paraffins, polyethylene oxides having a molecular weight greater than about 900, hydroxypropyl cellulose and cellulose derivatives.

7. The device of claim 1, wherein said coating has a coefficient of dynamic friction of less than 2.0.

8. The device of claim 1, wherein said coating has an elastic modulus, $G'$, greater than about 10,000 dynes/cm$^2$ at a frequency of 1 rad/sec and at room temperature, and the ratio of the viscous modulus, $G''$, to $G'$ is less than about 0.8 at a frequency of 1 rad/sec and at room temperature.

9. The device of claim 1, wherein said device is a dental floss.

10. The device of claim 1, wherein the alkyl group(s) provide(s) 3 to 75% by weight of the surfactant.

11. The device of claim 10, wherein the alkyl group(s) provide(s) 5 to 60% by weight of the surfactant.

12. A method for making a coated device for delivering chlorhexidine gluconate to the oral environment the method comprising:
   mixing aqueous chlorhexidine gluconate with a Solubilizing Glycol to form a mixture having less than 0.5 molar equivalents of deleterious quantities of salts, acids, and bases that would react with the chlorhexidine gluconate based on the amount of chlorhexidine glucanate in the mixture;
   adding a surfactant that contains both (a) hydrophilic group(s) capable of dispersing chlorhexidine gluconate and a glycol, and (b) an alkyl group(s) to form a coating composition;
   applying the coating composition to the device; and
   removing water at a temperature less than about 100° C.;
   wherein said coating on said coated device comprises no more than about 2% water by weight; and
   wherein said coating on said coated device contains no more than 200 ppm of PCA after four weeks at 45° C.

13. The method of claim 12 wherein water is removed before applying the coating composition to the device.

14. The method of claim 12 wherein water is removed alter applying the coating composition to the device.

15. The method of claim 12 wherein the surfactant is added before removal of water from the mixture.

16. The method of claim 12 wherein the surfactant is added after removal of water from the mixture.

17. The method of claim 12 wherein water is removed at a temperature less than about 80° C.

18. The method of claim 12 wherein water is removed under vacuum.

19. A method for making a coated device for delivering chlorhexidine gluconate to the oral environment, the method comprising:

freeze drying a composition of aqueous chlorhexidine gloconate, thereby removing substantially all water from chlorhexidine gluconate;

mixing said freeze-dried chlorhexidine gluconate with Solubilizing Glycol to form a mixture having less than 0.5 molar equivalents of deleterious quantities of salts that would react with the chlorhexidine gluconate based on the amount of chlorhexidine gluconate in the mixture;

adding a surfactant that contains both (a) hydrophilic group(s) capable of dispersing chlorhexidine gluconate and a glycol, and (b) an alkyl group(s) to form a coating composition; and applying the coating composition to the device;

wherein said coating on said coated device comprises no more than about 2% water by weight; and wherein said coating on said coated device contains no more than 200 ppm of PCA after four weeks at 45° C.

20. The method of claim 19, wherein the surfactant is added to the Solubilizing Glycol before mixing with chlorhexidine gluconate.

21. The method of claim 19, wherein the surfactant is added to the Solubilizing Glycol after the Solubilizing Glycol is mixed with chlorhexidine gluconate.

* * * * *

UNITED STATES PATENT AND TRADEMARK OFFICE
CERTIFICATE OF CORRECTION

PATENT NO.    : 6,733,745 B2
DATED         : May 11, 2004
INVENTOR(S)   : Rozzi, Sharon M.

It is certified that error appears in the above-identified patent and that said Letters Patent is hereby corrected as shown below:

<u>Column 6,</u>
Line 22, delete "75%  1.0%" and insert in place thereof -- 75%/1.0% --.

<u>Column 17,</u>
Line 49, delete "based an" and insert in place thereof -- based on --.

<u>Column 18,</u>
Line 38, delete "environment the" and insert in place thereof -- environment, the --.
Lines 44-45, delete "glucanate" and insert in place thereof -- gluconate --.
Line 59, delete "alter" and insert in place thereof -- after --.

<u>Column 19</u>
Line 59, delete "gloconate"and insert in place thereof -- gluconate --.

Signed and Sealed this

Seventeenth Day of August, 2004

JON W. DUDAS
*Acting Director of the United States Patent and Trademark Office*